United States Patent [19]

Horan

[11] Patent Number: 5,183,758
[45] Date of Patent: Feb. 2, 1993

[54] **PRODUCTION OF 7-CHLORO-3-METHOXY-2'-N-METHYLTETRACYCLINE WITH *ACTINOMADURA BRUNEA* ATCC 39216**

[75] Inventor: Ann C. Horan, Summit, N.J.

[73] Assignee: Schering Corporation, Kenilworth, N.J.

[21] Appl. No.: 528,006

[22] Filed: May 23, 1990

Related U.S. Application Data

[62] Division of Ser. No. 763,740, Aug. 8, 1985, abandoned.

[51] Int. Cl.⁵ .................. C12N 1/20; C12P 29/00; A61K 31/65
[52] U.S. Cl. .................. 435/252.1; 435/64; 435/825; 514/152
[58] Field of Search .............. 435/64, 252.1, 822, 435/825; 514/152

[56] References Cited

U.S. PATENT DOCUMENTS

| | | | |
|---|---|---|---|
| 3,502,660 | 3/1970 | Butler et al. | 260/351.3 |
| 3,849,493 | 11/1974 | Conover et al. | 260/351.3 |
| 3,862,225 | 1/1975 | Conover et al. | 260/351.3 |
| 4,752,605 | 6/1988 | Patel et al. | 514/152 |

FOREIGN PATENT DOCUMENTS

| | | | |
|---|---|---|---|
| 5108 | 7/1967 | France | 260/351.3 |
| 1553651 | 1/1969 | France | 260/351.3 |

*Primary Examiner*—David M. Naff
*Attorney, Agent, or Firm*—James R. Nelson; Henry C. Jeanette; Matthew Boxer

[57] ABSTRACT

An antibiotic complex is produced by the microorganism, *Actinomadura brunnea* NRRL 15216, ATCC 39216. A novel antibiotic 7-chloro-8-methoxy-2'-N-methyltetracycline, isolated from the antibiotic complex, is active against gram-positive and gram-negative aerobes.

1 Claim, No Drawings

PRODUCTION OF 7-CHLORO-3-METHOXY-2'-N-METHYLTETRACYCLINE WITH ACTINOMADURA BRUNEA ATCC 39216

This is a division, of application Ser. No. 06/763,740 filed Aug. 8, 1985, now abandoned.

BACKGROUND

This invention relates to a new tetracycline antibiotic, 7-chloro-8-methoxy-2'-N-methyltetracycline isolated from an antibiotic complex containing the new tetracycline antibiotic, which is produced by fermentation under controlled conditions using a biologically pure culture of the new microorganism *Actinomadura brunnea* ATCC 39216.

In a related, commonly-assigned, co-pending application which is U.S. Ser. No. 763,742 filed Aug. 8, 1985 now abandoned, filed on even date herewith, another new tetracycline, 7-chloro-8-methoxytetracycline produced by fermentation of a mutant of *A. brunnea, A. brunnea* var. antibiotica var. nov. ATCC 53108 and ATCC 53180 is disclosed.

In another related, commonly-assigned, copending application (Attorney's Docket No. 2381), now U.S. Pat. No. 4,752,605, filed on even date herewith, another new tetracycline, 7chloro-4a-hydroxy-8-methoxytetracycline produced by fermentation of *Dactylosporangium vescum* ATCC 39499 is disclosed.

SUMMARY OF INVENTION

The present invention embraces the biologically pure culture of the microorganism *Actinomadura brunnea* having the identifying characteristics of ATCC 39216 as well as mutants and variants thereof, said culture being capable of producing an antibiotic complex comprising the antibiotic compound of this invention, 7-chloro-8-methoxy-2'-N-methyltetracycline in a recoverable quantity upon fermentation under aerobic conditions in an aqueous medium containing assimilable sources of nitrogen and carbon.

The present invention is also directed to the novel antibiotic complex and to one component thereof namely 7-chloro-8-methoxy-2'-N-methyltetracycline, a compound represented by the formula:

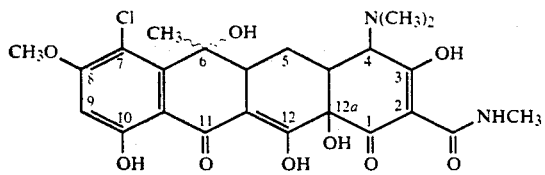

or a pharmaceutically acceptable salt thereof

The compound of this invention is systematically named 7-chloro-4-dimethylamino-8-methoxy1,4,4a,5-,5a,6,11,12a-octahydro-3,6,10,12,12a-pentahydroxy-6-methyl-1,11-dioxo-2-(2'-N-methylnaphthacene) carboxamide or simply 7-chloro-8-methoxy -2'-N-methyltetracycline.

The antibiotic complex of this invention is produced by cultivating a strain of *Actinomadura brunnea* having the identifying characteristics of ATCC 39216 in a pH and temperature controlled aqueous nutrient medium containing assimilable sources of nitrogen and carbon, under aerobic conditions until a composition of matter having substantial antibiotic activity and containing the compound of this invention is produced.

The present invention in addition is also directed to a pharmaceutical composition comprising an antibiotically effective amount of 7-chloro-8-methoxy -2'-N-methyltetracycline or a pharmaceutically acceptable salt thereof and a pharmaceutically acceptable carrier or diluent.

The present invention in addition is directed to a method of eliciting an antibiotic effect in a host, e.g. a mammal, having a susceptible infection which comprises administering to said host an antibiotically effective amount of the compound of this invention or a pharmaceutical composition thereof.

ISOLATION AND PURIFICATION OF THE ANTIBIOTIC COMPLEX

The antibiotic complex of this invention is produced when the elaborating organism, *Actinomadura brunnea* having the identifying characteristics of ATCC 39216 is grown in an appropriate nutrient medium.

The antibiotic complex of this invention may be isolated from the fermentation broth by solvent extraction, and filtration and employing the following procedure:

(a) Adjust the pH of the whole broth to 2 and filter;
(b) Adjust the pH of the filtrate to 8.5;
(c) Extract the filtrate using two volumes of organic solvent (e.g. ethyl acetate) each time for each volume of broth;
(d) Combine the organic solvent extracts and remove the organic solvent by stripping to yield a solid residue;
(e) Dissolve the residue in acetone and filter off the insolubles;
(f) Add a mixture of 1:4 (v/v) ethyl ether: hexane to the filtrate until a precipitate forms;
(g) Collect the precipitate.

Using the above procedure, 100 mg of antibiotic complex of this invention were obtained from 3.5 L of fermentation broth. Since the antibiotic complex of this invention is made up at least two dissimilar components, no meaningful physico-chemical data can be determined for the complex.

SEPARATION OF THE ANTIBIOTIC COMPLEX

The antibiotic complex of this invention is made up of at least two active components, one of which has been isolated and characterized as the novel 8-substituted tetracycline of this invention, 7-chloro-8-methoxy -2'-N-methyltetracycline.

The active antibiotics, including the 8-methoxytetracycline of this invention can be isolated from the antibiotic complex of this invention (as the HCl salt) by chromatography using, for example, a Sephadex G-25 gel column. The eluate (dilute aqueous HCl) from the column was monitored by determining the activity of each fraction against *S. aureus* and *E. coli*. The desired active fractions were combined and lyophilized to give a light yellow powder which was crystallized from methylene chloride:hexane to give the novel 7-chloro-8-methoxy-2'-N-methyltetracycline.

The physical and spectroscopic data for 7-chloro-8-methoxy-2'-N-methyltetracycline are presented in Table I below.

TABLE I

Physico-Chemical Data for 7-Chloro-8-Methoxy-2'N-Methyltetracycline (a) The data for the chemical analysis are the following:

Formula: for $C_{24}H_{27}O_9N_2Cl\cdot HCl$

| | C | H | N | Cl |
|---|---|---|---|---|
| Calc: | 51.6 | 5.05 | 5.02 | 12.5 |
| Found: | 48.7 | 5.03 | 4.11 | 11.2 |

(b) The EI-MS yielded an $M^-$ peak at 522.1414. This corresponds to the formula $C_{24}H_{27}O_9N_2Cl$ which calculates for the exact mass, 522.1405.
(c) The ultraviolet absorption maxima in methanol are: 234 ($\epsilon$ 17,400), 250 ($\epsilon$ 15,700) and 374 nm ($\epsilon$ 19,500). The ultraviolet absorption maxima shift to 232 ($\epsilon$ 15,800), 258 ($\epsilon$ 17,600) and 369 nm ($\epsilon$ 18,300) upon the addition of acid. The maxima shift to 240 ($\epsilon$ 20,400) and 281 nm ($\epsilon$ 14,600) and 385 nm ($\epsilon$ 18,900) upon the addition of base.
(d) The infrared spectrum in KBr has the following characteristic absorption bands: 3420 (br), 1660, 1608, 1574,1432, 1414, 1380, 1240, and 1210 $cm^{-1}$.
(e) The $^{13}$C—NMR in DMSO-$d_6$ is presented in Table II.

TABLE II $^{13}$C—NMR in DMSO-$d_6$ for 7-Chloro-8-Methoxy-2'-N-Methyltetracycline

| Carbon | Resonance (ppm) |
|---|---|
| C-1 | 193.1 |
| C-2 | 96.5 |
| CONHCH$_3$ | 169.9 |
| C-3 | 186.3 |
| C-4 | 68.0 |
| N(CH$_3$)$_2$ | 41.5$^a$ |
| C-4a | 34.8 |
| C-5 | 26.9 |
| C-5a | 42.3$^a$ |
| C-6 | 73.3 |
| CH$_3$—C-6 | 20.4 |
| C-6a | 148.5 |
| C-7 | 111.6 |
| C-8 | 163.2$^b$ |
| C-9 | 100.0 |
| C-10 | 161.8 |
| C-10a | 106.6 |
| C-11 | 190.6 |
| C-11a | 105.4 |
| C-12 | 174.1 |
| C-12a | 73.6 |
| O-CH$_3$ | 56.9 |
| N-CH$_3$ (2'-N) | 26.5 | a - indicates peaks buried under DMSO peak, but observed when spectrum was run in D$_2$O/Dioxane
b - The resonance of C-8 carbon in the $^{13}$C-NHR of 7chlorotetracycline appears at 140 ppm. The shift of C-8 carbon in 7-chloro-8-methoxy-2'-N-methyltetracycline to 163.2 is indicative of the presence of the novel methoxy substituent.

Based on the above data, the structure of the compound of this invention (without specifying stereochemistry) is the following:

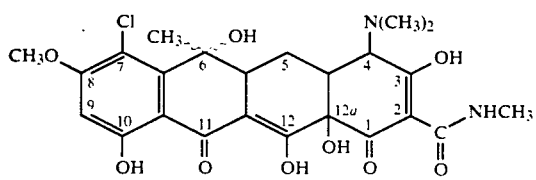

Biological Properties of Antibiotic Complex and 7-Chloro-8-Methoxy-2'-N-Methyltetracycline The antibiotic complex of this invention containing at least two components, including 7-chloro-8-methoxy-2'-N-methyltetracycline is active against a variety of gram-positive and gram-negative bacteria when tested in vitro.

In comparative in-vitro antibacterial activity tests using 7-chloro-8-methoxy-2'-N-methyltetracyline and tetracycline performed via conventional microtiter dilution methods in Mueller-Hinton broth, 7-chloro-8-methoxy -2'-N-methyltetracycline showed activity against 91 gram-positive tetracycline-susceptible organisms with a Geometric Mean Minimum Inhibitory Concentration (GMM mcg/mL) of 0.36, which is similar to the GMM for tetracycline (0.46). The compound of this invention had a GMM of 33 against 23 gram-negative tetracycline-susceptible organism compared to a GMM of 2.3 for tetracycline. The 23 gram-negative organisms included nine strains of *E. coli*, eight of Klebsiella, four of Enterobacter and two of Salmonella. The compound of this invention had a GMM of 0.86 against nine Methicillin-resistant Staphylococci, a GMM of 0.48 against 54 Methicillin-susceptible organisms, a GMM of 0.15 against 25 Streptococci (including Groups A, B, C, G, *S. pneumoniae, S. viridans, S. faecium* and *S. faecalis*), and a GMM of 0.41 against 10 strains of *Bacteroides fragilis* (tested in Mueller-Hinton agar with 5% sheep blood).

The present invention contemplates a method of eliciting an antibacterial effect in a host, e.g., a warm-blooded mammal such as a human being having a susceptible bacterial infection which comprises administering to said host an antibiotically effective amount of 7-chloro-8-methoxy-2'-N-methyltetracycline or a pharmaceutical composition thereof. By the term "eliciting" is meant treating or preventing susceptible bacterial infection.

The methods of this invention are implemented using pharmaceutical compositions comprising a pharmaceutically acceptable carrier and a therapeutically effective quantity of 7-chloro-8-methoxy-2'-N-methyltetracycline or a pharmaceutically acceptable salt thereof.

The preferred pharmaceutically acceptable salts are the acid addition salts. Pharmaceutically acceptable acid addition salts of 7-chloro-8-methoxy-2'-N-methyltetracycline are those formed from strong acids containing pharmaceutically acceptable anions, such as hydrochloride, hydrobromide, hydrogen sulfate and trichloroacetate. Acid addition salts may also be formed with carboxylic acids having 2-18 carbon atoms such as aliphatic, cycloaliphatic, aromatic and heterocyclic carboxylic acids, including dicarboxylic acids. Exemplary of such acids are acetic, propionic, stearic, tartaric, maleic, cyclopropylcarboxylic, cyclopentylcarboxylic, adamantioic, furic, nicotinic, thenoic, picolinic, benzoic, phenylacetic and the like.

The antibiotic of this invention may be combined with any suitable pharmaceutical carrier and administered orally, parenterally or topically in a variety of formulations. For oral administration, the antibiotic of this invention may be compounded in the form of tablets, capsules, elixirs or the like. Tablets and capsules may contain such excipients as starch or lactose; liquid forms may contain coloring or flavoring agents. Topical preparations may be in the form of creams, hydrophobic and hydrophylic ointments, or aqueous, non-aqueous or emulsion-type lotions. Typical carriers for such formulations are water, oils, greases, polyesters and polyols. Parenteral formulations, e.g., injectable dosage forms, are usually liquids such as solutions or suspensions, with typical carriers being distilled water and saline solution.

Oral administration of the compound of this invention is preferred.

The dose to be administered in any particular dosage form will be determined by the attending clinician after consideration of various factors, such as the age and condition of the animal species being treated, the susceptibility of the infecting organism to the antibiotic, the stage and severity of the infection.

Generally, the oral dosage administered is from about 1.0 mg to about 25 mg per kilogram of body weight per day, in single or divided doses with about 5 mg kilogram to about 10 mg per kilogram being preferred.

Generally, the topical dosage administered is from about 1% to about 5% in single or divided doses, with about 1% to about 3% being preferred.

Generally, the parenteral dosage administered us from about 100 mg to about 2000 mg per day, in single or divided doses, with about 500 mg to about 1000 mg being preferred.

In treating certain patients with the compounds of this invention, it is possible to include other pharmaceutically active ingredients in the same dosage unit.

The Microorganism

The microorganism used for the production of antibiotic complex of this invention is a biologically pure culture of *Actinomadura brunnea* ATCC 39216.

A culture of this microorganism has been deposited with the Northern Utilization and Research Division, Agriculture Research Service, U.S. Department of Agriculture in Peoria, Ill. where it has been assigned accession number NRRL 15216. Subcultures of *Actinomadura brunnea* NRRL 15216 are available to the public without restriction from the aforementioned agency. A culture of this microorganism has been made a part of the collection of the American Type Culture Collection (ATCC) in Rockville, Md. where it has been assigned accession number ATCC 39216. Subcultures of *Actinomadura brunnea* ATCC 39216 are available to the public without restriction. Use of the microorganism is dependent on U.S. Patent Laws.

The microorganism was isolated from a sample of soil collected near Phoenix, Ariz. It had been characterized and found to have the microscopic, macroscopic, and whole cell hydrolysis properties of the genus Actinomadura.

Description of the Producing Strain: Actinomadura brunnea sp. nov NRRL 15216, ATCC 39216

The taxonomic methods used herein are those cited by R. E. Gordon and V. Blanchard, "Some criteria for the recognition of *Nocardia madura*", *J. Gen. Microbiol.*, 45, pp 355-364 (1966), by Luedemann and in Brodsky, in "*Micromonospora carbonacea* sp. nov, an everninomicin-producing organism", Antimicrob Agents Chemotherapy, pp 47-52, 1964; by Horan and Brodsky, "A Novel Antibiotic-Procucing Actinomadura, *Actinomadura kijaniata* sp. nov.", *International Journal Syst. Bacterial.*, Vol. 32, pp 195-200, 1982; by Becker et al, "Chemical Composition of Cell Wall Preparations from Strains of Various Genera of Aerobic Actinomycetes", *Applied Microbiology*, Vol. 13, pp 236-243, 1966; by Lechevalier and Lechevalier, "Chemical Composition as a Criterion in the Classification of Aerobic Actinomycetes", *International Journal Syst. Bacterial.* Vol. 20, ppg 487-493, 1970; by Shirling and Gottlieb, "Methods for Characterization of Streptomyces Species", *International Journal Syst. Bacterial*, Vol. 16, ppg 313-340, 1966; and Waksman, *The Actinomycetes*, Vol. 2, (The Williams & Wilkins Co., Baltimore, Md., 1961).

TABLE III

Macroscopic and Microscopic Characteristics of *Actinomadura brunnea* NRRL 15216, ATCC 39216

| Macroscopic | Microscopic |
|---|---|
| Aerial Mycelia are formed | |
| Good growth occurs after 14-21 days at 30° C. on most rich organic media, and yellow-brown to brown diffusible pigments are formed. White to pale pink aerial mycelia are formed on yeast extract-malt extract (ISP-2), tyrosine (ISP-7) and tomato paste-oatmeal agars. Weak growth occurs on glycerol-asparagine agar. Vegetative mycelial pigments usually range in color from tan to cocoa brown except on glycerol-asparagine where the vegetative mycelia are rose. | Abundant, long, branching aerial mycelia, 0.5 to 0.8 microns in diameter are formed on water agar after 10 to 14 days at 30° C. The aerial mycelia fragment into long, straight to flexous chains of greater than 20 eleptical spores, 0.8 to 1.2 microns in diameter by 1.0 to 2.0 microns in length. |

The culture characteristics of the microorganism *Actinomadura brunnea* NRRL 15216, ATCC 39216 on various standard media are reported in Table IV. In the description of the growth characteristics of the microorganism in Table IV, two color designators are employed. The first is a color name taken from the "Descriptive Color Name Dictionary" by Taylor, Knoche and Granville published by the Container Corporation of America (1950) U.S.A., with a color chip number corresponding to the color name, the chip number being taken from "The Color Harmony Manual", 4th Edition, 1958, also published by the Container Corporation of America. The second designator consists of a color name and number which refers to the synonym and near synonym found in the National Bureau of Standards, Circular 553, November 1, 1965 (U.S.A.).

Growth of the microorganism, *Actinomadura brunnea* NRRL 15216, ATCC 39216 on various carbon compounds is reported in Table V.

Physiologic characteristics of the microorganism *Actinomadura brunnea* NRRL 15216, ATCC 39216 are reported in Table VI.

A comparison of the characteristics of *Actinomadura brunnea* NRRL 15216, ATCC 39216 with those of other species of Actinomadura is listed in Table VII.

Whole cell analysis of the microorganism *Actinomadura brunnea* NRRL 15216, ATCC 39216 found mesodiaminopimelic acid as the characteristic cell wall amino acid, trace amounts of the L, L isomer and madurose (3-0methyl-D-galactose) as the characteristic whole cell sugar.

Growth of the microorganism occurs from 27° to 40° C. on yeast-dextrose agar. Poor growth occurs at 45° C., with optimum growth at from 27° to 35° C.

TABLE IV

**GROWTH CHARACTERISTICS OF *ACTINOMADURA BRUNNEA* NRRL 15216, ATCC 39216 ON VARIOUS DESCRIPTIVE MEDIA**[a,b]

| Medium | Growth Characteristics |
|---|---|
| Bennett's Agar | G: ++, Moderate<br>S: Flat, raised edges<br>AM: Present; moderate, white<br>DFP: Present; light brown<br>C: g 3 li, beaver |
| Czapek Sucrose Agar | G: ++, Moderate<br>S: Slightly raised<br>AM: Present; fair, white<br>DFP: Absent<br>C: g 5 gc, peach tan |
| Glucose Asparagine Agar | G: +++, Good<br>S: Raised, folded<br>AM: Absent<br>DFP: Absent<br>C: g 4 le, maple |
| Glycerol Asparagine Agar (ISP #5) | G: +, Fair<br>S: Flat, smooth<br>AM: Present; sparse, white<br>DFP: Absent<br>C: g 6 ia, brite coral rose |
| Nutrient Agar | G: ++, Moderate<br>S: Flat to raised<br>AM: Present; sparse, white<br>DFP: Absent<br>C: g 3 lg, adobe brown |
| Peptone Glucose Agar | G: +++, Good<br>S: Raised, folded<br>AM: Absent<br>DFP: Absent<br>C: g 4 ic, suntan |
| Potato Dextrose Agar | G: +++, Good<br>S: Raised, folded<br>AM: Absent<br>DFP: Absent<br>C: g 5 gc, peach tan |
| Emerson's Agar | G: +++, Good<br>S: Raised, folded<br>AM: Present; sparse, white<br>DFP: Present; brown<br>C: g 4 lg, toast tan |
| NZA Glucose Agar | G: +++, Good<br>S: Raised, ridged<br>AM: Absent<br>DFP: Present; yellow brown<br>C: g 3 lg, adobe brown |
| Yeast Extract Glucose Agar | G: +++, Good<br>S: Raised, folded<br>AM: Present; sparse, white<br>DFP: Present; brown<br>C: g 5 ni cocoa brown |
| Tomato Paste-Oatmeal Agar | G: +++, Good<br>S: Raised, folded<br>AM: Present; abundant, white<br>DFP: Present; gray<br>C: g 3 nl, dark brown |
| Yeast Extract Malt Extract Agar (ISP #2) | G: +++, Good<br>S: Raised, folded<br>AM: Present; abundant, white<br>DFP: Present; brown<br>C: g 5 ni, cocoa brown |
| Oatmeal Agar | G: +, Fair<br>S: Flat, smooth<br>AM: Present; moderate, pale pink<br>DFP: Absent<br>C: g 4 gc, nude tan |
| Inorganic Salts-Starch Agar (ISP #4) | G: ++, Moderate<br>S: Flat, smooth<br>AM: Present, moderate, white<br>DFP: Absent<br>C: g 5 le, rust tan |
| Starch Agar (W #21) | G: ++, Moderate<br>S: Flat, smooth<br>AM: Present; sparse, white<br>DFP: Absent<br>C: g 5 ie, copper tan |
| Calcium Maleate Agar | G: ++, Moderate |
| (W #7) | S: Slightly raised, folded<br>AM: Absent<br>DFP: Absent<br>C: g 5 ic, light persimmon |
| Peptone Iron Agar | G: +++, Good<br>S: Raised, folded<br>AM: Absent<br>DFP: Absent<br>C: g 3 ie, camel |
| Tyrosine Agar (ISP #7) | G: +++, Good<br>S: Raised, folded<br>AM: Present; abundant, white to pale pink<br>DFP: Present; light brown<br>C: g 4 lg, toast brown |
| Starch Yeast Agar | G: ++, Moderate<br>S: Raised, folded<br>AM: Present; abundant, white<br>DFP: Present; yellow brown<br>C: g 4 nl, dark brown |

[a] Observations made after 14-21 days at 30° C.
[b] G = Growth; S = Surface Characteristics; AM = Aerial Mycelia; DFP = Diffusible Pigments; and C = Color.

TABLE V

**CARBOHYDRATE UTILIZATION[1] OF *ACTINOMADURA BRUNNEA* ATCC 39216**

| Utilization of: | Result |
|---|---|
| Adonitol | +++Good |
| D-Arabinose | ++, Moderate |
| L-Arabinose | +++Good |
| Cellibiose | +++Good |
| Dextrin | +++Good |
| Dulcitol | −, Poor |
| Erythritol | −, Poor |
| Fructose | −, Poor |
| L-Fucose | +++Good |
| Galactose | −, Poor |
| Glucose | +++Good |
| α-m-d-glucoside | −, Poor |
| m-β-d-glucoside | −, Poor |
| Glycerol | +++Good |
| Inositol | ++, Moderate |
| Inulin | −, Poor |
| Lactose | −, Poor |
| Maltose | +++Good |
| Mannitol | −, Poor |
| Mannose | +++Good |
| Melibiose | −, Poor |
| Melizitose | −, Poor |
| Raffinose | −, Poor |
| Rhamnose | ++, Moderate |
| Ribose | +++Good |
| Sucrose | +++Good |
| Trehalose | +++Good |
| D-Xylose | −, Poor |

[1] Medium of Luedemann and Brodsky (Antimicrob. Ag. Chemoth. 1965)

TABLE VI

**PHYSIOLOGIC CHARACTERISTICS OF *ACTINOMADURA BRUNNEA* ATCC 39219**

| Test | Result |
|---|---|
| Utilization of Organic Acids | |
| Acetate | + |
| Benzoate | − |
| Butyrate | + |
| Citrate | + |
| Formate | + |

TABLE VI-continued

PHYSIOLOGIC CHARACTERISTICS OF ACTINOMADURA BRUNNEA ATCC 39219

| Test | Result |
|---|---|
| Glucuronate | − |
| Glutamate | − |
| Lactate | − |
| Proprionate | ± |
| Succinate | + |
| Pyruvate | + |
| Growth in the Presence of 50 mcg/ml | |
| Gentamicin | + |
| Sisomicin | − |
| Neomycin | + |
| Kanamycin | + |
| Stretomycin | ± |
| Rosaramicin | − |
| Erythromycin | + |
| Lincomycin | ± |
| Clindamycin | + |
| Tetracycline | ± |
| Penicillin G | + |
| Cephalothin | + |
| Rifamycin | ± |
| Everninomicin | − |
| Hydrolysis of | |
| Adenine | − |
| Hypoxanthine | − |
| Tyrosine | − |
| Xanthine | − |
| Xylan | − |
| Casein | ± |
| Gelatin | − |
| Starch | ± |
| Hippurate | − |
| Esculin | + |
| Breakdown of | |
| Urea | + |
| Allantoin | − |
| Nitrate to Nitrite | − |
| Growth at | |
| 27° C. | ++, Moderate |
| 35° C. | +++Good |
| 40° C. | ++, Moderate |
| 45° C. | ±, Poor |
| Survival | |
| 50° C./8 hr. | + |
| Growth in the Presence of | |
| NaCl 1% | +++Good |
| 2% | ++, Moderate |
| 3% | ++, Moderate |
| 4% | ±, Poor |
| Formation of | |
| $H_2S$ | − |
| Melanin | − |
| Breakdown of | |
| Loefflers Serum | − |
| Dorset's Egg | − |

TABLE VII

COMPARATIVE CHARACTERISTICS OF SPECIES OF ACTINOMADURA
Taxonomy

| Species | Spore Chain | Spore Surface | Aerial Mycelia Color | Vegatative Mycelia Color |
|---|---|---|---|---|
| Actinomadura brunnea ATCC 39216 | Fragmentation of entire aerial mycelia into chains of spores. Straight to flexous, long | Smooth | White to pale pink | Tan to cocoa brown |
| A. citrea ATCC 27887 | Straight to hooked, short | Uneven | Yellow-blue | Lemon yellow |
| A. flava ATCC 29533 | Fragmentation of entire aerial mycelia into chains of spores. Straight, long | Smooth | Rarely formed | Lemon-yellow-yellow-brown |
| A. melliaura ATCC 39691 | Straight open, short to long | Smooth brown | White | Tan to Yellow |
| A. helvata ATCC 27295 | Closed spirals, short | Smooth | White to pink | Yellow brown |
| A. kijaniata ATCC 31588 | Fragmentation of entire aerial mycelia into chains of spores. Flexous spirals, long | Smooth green | White to pale | Dark green |
| A. macra ATCC 31286 | Straight to flexous, short | Smooth | Grayish | Cream to gray |
| A. madurae ATCC 19425 | Curls to hooks, short | Smooth | Rarely formed, white to pink | Pink to red |
| A. malachitica ATCC 27888 | Loose spirals, short | Smooth | Rarely formed, pale green | Cream |
| A. pelletieri ATCC 14816 | Curls to hooks, short | Smooth | Rarely formed, White to pink | Pink to red |
| A. pusilla ATCC 27296 | Closed spirals, short | Smooth | White to pink | Brownish-gray blue-black |
| A. roseoviolacea ATCC 27297 | Hooks to closed spirals, short | Smooth to Uneven | White to pink | Red to volet |
| A. rubra ATCC 27031 | Hooks to spirals, short | Smooth to Uneven | Rarely formed, white to pink | Brick red |
| A. spadix ATCC 27298 | Hooks to closed spirals, short | Smooth | Grayish | Gray-brown |
| A. verrucosospora ATCC 27299 | Hooks to spirals | Uneven | Grayish-blue | Pink |

TABLE VII-continued
COMPARATIVE CHARACTERISTICS OF SPECIES OF ACTINOMADURA
Taxonomy

| Species | Meso-Diamino-Pimelic Acid and Madurose | Antibiotic Activity | Hydrolysis of Xanthine | Utilization of Methyl-B-D-Glucoside | Mannitol |
|---|---|---|---|---|---|
| Actinomadura brunnea ATCC 39216 | − | + | − | − | − |
| A. citrea ATCC 27887 | + | − | − | − | + |
| A. melliaura ATCC 29533 | + | + | − | − | + |
| A. melliaura ATCC 39691 | + | + | − | + | + |
| A. helvata ATCC 27295 | + | − | − | − | + |
| A. kijaniata ATCC 31588 | + | + | + | + | − |
| A. macra ATCC 31286 | + | + | − | − | − |
| A. madurae ATCC 19425 | + | + | − | − | + |
| A. malachitica ATCC 27888 | + | − | − | − | + |
| A. pelletieri ATCC 14816 | − | + | − | − | − |
| A. pusilla ATCC 27296 | + | + | − | + | − |
| A. roseoviolacea ATCC 27297 | − | − | − | − | + |
| A. rubra ATCC 27031 | − | − | − | − | + |
| A. spadix ATCC 27298 | − | − | − | − | + |
| A. verrucosospora ATCC 27299 | − | −,+ | − | − | + |

Based on the cell wall analysis and morphologic characteristics reported in Tables III and VII, the microorganism of this invention is categorized as a species of the genus Actinomadura. Of the named, deposited strains of this genus listed in Table VII, the microorganism of this invention shares vegetative mycelia pigmentation with the species *A. helvata*, *A. flava* and *A. melliaura*.

The microorganism of this invention, *Actinomadura brunnea* ATCC 39216 (hereinafter *A. brunnea*), may be distinguished from the above listed species of Actinomadura by comparisons of the characteristics listed in Table VII.

*A. brunnea* differs from *A. helvata* (1) in morphology of the spore-bearing hyphae: *A. helvata* forms short, coiled chains of spores as side branches along the length of the aerial mycelium; *A. brunnea* forms abundant long, branching aerial mycelia which fragment into long, straight to flexous chains of greater than 20 elliptical spores; (2) in the utilization of mannitol: *A helvata* utilizes mannitol, but *A. brunnea* does not; and (3) in antibiotic production: *A brunnea* produces the novel 8-substituted tetracycline antibiotic, but *A. helvata* exhibits no antibiotic activity.

*A. brunnea* differs from *A. flava* (1) in the formation of aerial mycelia: *A. flava* rarely forms aerial mycelia when compared to *A. brunnea;* and (2) in the utilization of mannitol: *A. flava* utilizes mannitol while *A. brunnea* does not.

*A. brunnea* differs from *A. melliaura* (1) in morphology: *A. melliaura* forms short to long spore chains, and the terminal end of the aerial mycelium forks into two sporophores bearing a straight chain of spores; in the utilization of methyl-B-D-glucoside and mannitol by *A. melliaura* but not by *A. brunnea* and in the type of antibiotic production: *A. melliaura* produces a fused indole aminoglycoside while *A. brunnea* produces the novel 7-chloro-8-methoxy-2'N-methyltetracycline of this invention.

On the basis of these morphological, physiological and culture characteristics, as well as on the production of the novel 8-substituted chlortetracycline of this invention, the microorganism of this invention is considered to represent a distinct, new species of the genus Actinomadura. It's proposed that the microorganism be designated *Actinomadura brunnea*, Horan and Brodsky sp. nov. The species name selected refers to the brown vegetative mycelial pigments formed.

It is understood that in accordance with the rules of Nomenclature of Bacteria (S.P. Lapage et al. Ed. 1975, *International Code of Nomenclature of Bacteria*, 1976 revision) *A. brunnea* is the type strain and that should another strain be found, the type strain would also be the type subspecies.

FERMENTATION OF THE MICROORGANISM

Antibiotic complex of this invention is produced when the elaborating microorganism, *Actinomadura brunnea* is grown in an aqueous nutrient medium under submerged aerobic conditions at a temperature of about 27° C. to 40° C., preferably at from 27° C. to 35° C., and at a pH of from about 6.5 to 8.0 with agitation until substantial antibiotic activity is imparted to the medium. Temperature studies indicate that the organism grows rapidly at 30° C. Therefore, the fermentation is preferably conducted employing a single temperature pattern of 30° C. for the first 48 hours as well as for the period 24 to 96 hours. The fermentation is generally conducted from 3 to 7 days although preferably for 4 days. To determine when peak antibiotic production has been reached, samples of the medium were assayed every 24 hours for antibiotic content by bioassay of the whole broth against *S. aureus* ATCC 209P (pH 7.0) and *E. coli* ATCC 10536 (pH 8.0). The growth of the organism (packed cell volume), pH and dissolved oxygen levels were determined either intermittantly or continuously.

As nutrient medium, there is employed any suitable medium containing a source of carbon, for example an assimilable carbohydrate, and a source of nitrogen, for example an assimilable nitrogenous or proteinaceous material.

The medium employed for the fermentation contained NZ-Amine A (an enzymatic hydrolysate of casein) and soluble starch as the major sources of nitrogen and carbon. Under these conditions the microorganism produced the antibiotic complex of this invention containing at least 2 components as determined by bioautography against both *S. aureus* and *E. coli* of the complex after development of a thin layer chromatography plate in 2:2:1 (v/v/v) chlorofrom: methanol: pH 3.5 acetate buffer.

The foregoing media are exemplary of the nutrients utilized by *Actinomadura brunnea* to produce the antibiotic complex of this invention. However, it is obvious to those skilled in the fermentation art that a wide range of nutrients obtained from a number of suppliers may be substituted for the foregoing, and that generally good growth and antibiotic production can be obtained, such nutrients being the functional equivalent to those set forth herein.

The fermentation is generally conducted by initially sterilizing the fermentation medium prior to the addition of the inoculum.

The pH of the fermentation medium is generally maintained at from 6.5 to 8.0, a pH of from 6.5 to 7.5 being preferred. Prior to sterilization, the pH of the medium is usually adjusted to 6.7 and prior to inoculation the pH is usually adjusted to 7.5.

The fermentation was initiated by addition of the inoculum to the broth. Generally, inoculum volume is 5% of total broth volume. The inoculum is prepared by addition of a sample of the frozen whole broth to an appropriate medium. A particularly preferred medium comprises beef extract, 0.3%; tryptone, 0.5; dextrose, 0.1%; potato starch, 2.4%; yeast extract, 0.5%; and calcium carbonate, 0.2%. The pH of the inoculum medium is adjusted to 7.5 prior to sterilization. The inoculum stage of the fermentation usually requires from 24 to 120 hours with 1 to 2 days preferred and is generally conducted at about 30° C.

EXAMPLE 1

Preparation of Antibiotic 81-47 Complex

A. Inoculum Preparation

1) Initial Stage

Prepare ten 250 mL Erlenmeyer flasks with 50 mL of the following germination medium:

| | | |
|---|---|---|
| Beef Extract | 3 | g |
| Tryptone | 5 | g |
| Yeast Extract | 5 | g |
| Dextrose | 1 | g |
| Potato Starch | 24 | g |
| Tap Water | 1000 | mL |

Adjust the pH of the germination broth to 7.5. Sterilize the broth and after cooling add 2.5 mL of a frozen whole broth sample from a previously prepared inoculum to the broth. Incubate at 30° C. with continual agitation at 300 rpm for 48 hours.

2) Second Stage

Transfer 25 ml of the first stage germination broth to each of twenty 2-liter Erlenmeyer flasks, each containing 500 mL of the same germination medium and which had been previously pH adjusted and sterilized. Incubate at 30° C. with continual agitation at 300 rpm for 48 hours.

B. Fermentation

In 14 L fermentors, add 10 L of the following medium:

| | |
|---|---|
| Yeast Extract | 5 g |
| Casein Hydrolysate | 5 g |
| Cerelose | 10 g |
| Soluble Starch | 20 g |
| Calcium Carbonate | 4 g |
| Cobalt (II) Chloride | $2.4 \times 10^{-4}$ g |
| Tap water | 1000 mL |

Adjust the pH of the medium to 6.7 and then sterilize the medium. After sterilization, adjust the pH of the medium to 7.0 with a sterile alkaline solution. Inoculate the fermentation medium with 5% volume of the second stage inoculum preparation of Step A. Incubate the fermentation mixture at 30° C. with 0.35 VVM of air and 350 rpm agitation for about 96 hours.

C. Isolation

Adjust the pH of the whole fermentation broth of step B to 2 and filter the insolubles. Adjust the pH of the filtrate to 8.5 Extract 3.5 L of the filtrate twice with 3.5 L of ethyl acetate. Combine the ethyl acetate solutions, dry them over anhydrous sodium sulfate and remove the solvent by stripping to give a residue. Dissolve the dry residue in 35 mL of acetone and then add 350 mL of a 1:4 (v/v) mixture of ethyl ether:hexane until a precipitate results. Filter the precipitate and dry in a vacuum to give of the (crude) antibiotic complex of this invention.

EXAMPLE 2

Separation of Antibiotic Complex—Isolation of 7-chloro-8-methoxy-2'-N-methyltetracycline Dissolve a 100 mg portion of the crude antibiotic complex of Example 1C in 10 mL of 0.02N HCl. Adsorb the solution so formed on a 2.54 cm × 63.5 cm gel column containing 300 mL of Sephadex G-25 filtration gel (medium; dry particles size 50–150 mm). (Sephadex G-25 is a cross-linked dextran, a polysaccharide, available from Pharmacia Fine Chemicals, Inc. Piscataway, N.J.) Elute the column with 0.02N HCl at a flow rate of about 3.0 mL per minute. Monitor the activity of each fraction (10 mL) against *S. aureus* ATCC 209P (pH 7.0) and *E. coli* ATCC 10536 (pH 8.0) using a disc diffusion assay. Spot the active fraction on thin layer chromatography plates developed in a 2:2:1 (v/v/v) chloroform:methanol:pH 3.5 acetate buffer. Detect the antibiotic components by bioautography against both *S. aureus* and *E. coli*.

Obtain the novel 7-chloro-8-methoxy-2'-N-methyltetracycline by combining fractions 26 to 32. Lyophilize the pooled fractions to provide a light yellow powder. Crystallize a portion of the light yellow powder from a 30:70 (v/v) methylene chloride:hexane mixture to provide the title compound as a yellow powder having physico-chemical data summarized in Table 1.

Formulations

EXAMPLE 3

Parenteral Formulation

Per vial:7-chloro-8-methoxy-2'-N-methyltetracycline (hereinafter "drug") as a sterile powder. Unit dosages, maybe 100 mg, 200 mg, 500 mg, 1 g and 2 g. Add sterile water for injection U.S.P. or bacteriostatic water for injection U.S.P., for reconstitution.

EXAMPLE 4

Capsule Formulation

| Item No. | Ingredient | mg/capsule | mg/capsule |
|---|---|---|---|
| 1 | Drug | 100 | 200 |
| 2 | Lactose | 122 | 244 |
| 3 | Corn Starch, Dried | 25.5 | 51 |
| 4 | Magnesium Stearate | 2.5 | 5 |
|   |   | 250 mg | 500 mg |

Method

Mix Item Nos. 1, 2, and 3 in a suitable mixer for 10–15 minutes. Add Item No. 4 and mix for 1–3 minutes. Fill the above mixture in two-piece hard gelatin capsules of required size.

EXAMPLE 5

Tablet Formulation

| Item No. | Ingredient | mg/capsule | mg/capsule |
|---|---|---|---|
| 1 | Drug | 125 | 250 |
| 2 | Lactose | 93.75 | 187.5 |
| 3 | Corn Starch (as a 10% Paste) | 5 | 10 |
| 4 | Corn Starch, Dried | 25 | 50 |
| 5 | Magnesium Stearate | 1.25 | 2.5 |
|   |   | 250 mg | 500 mg |

Method

Mix Item Nos. 1, 2 and a portion of Item No. 4 in a suitable mixer for 10–15 minutes. Granulate the mixture with Item No. 3. Pass the wet granulation through a coarse screen (e.g., $\frac{1}{4}$") if needed, and dry the wet granules. Mill the dried granules using a suitable milling machine. Add Item No. 5 and the remaining amount of Item No. 4, with the dried granules in a suitable blender. Mix for 5–10 minutes. Compress the mixture into the tablets of required shape and size on a rotary tablet machine. The tablets may be coated using standard coating procedures.

EXAMPLE 6

Topical Formulation

| Item No. | Ingredient | mg/g |
|---|---|---|
| 1 | Drug | 25 |
| 2 | Ethyl Alcohol | 400 |
| 3 | Hydroxypopyl Cellulose | 15 |
| 4 | Polyethylene Glycol 400 | 560 |

Mix Item Nos. 1, 2 and 4 in a suitable mixer. Stir vigorously and charge Item No. 3. Maintain stirring until uniformity is achieved.

EXAMPLE 7

Oral Powder for Reconstitution (I)

Part A (Powder Formulation)

| Item No. | Ingredient | mg/g |
|---|---|---|
| 1 | Drug | 46.3 |
| 2 | Flavor(s) | q.s. |
| 3 | Colorant | q.s. |
| 4 | Preservative | q.s. |
| 5 | Buffer Agents | q.s. |
| 6 | Sugar | q.s. |
|   | To make | 1.0 g |

Mix Item Nos. 1, 2, 3, 4 and 5 thoroughly. Charge Item No. 6 and mix until uniformity is achieved.

Part B (Reconstitution)

Charge 54 g of above formulated powder into a proper container and add enough water to make up 100 ml. Shake well after the addition of water. Each 5 ml (1 teaspoonful) will then contain drug equivalent to 125 mg.

EXAMPLE 8

Oral Powder for Reconstitution (II)

Part A (Powder Formulation)

| Item No. | Ingredient | mg/g |
|---|---|---|
| 1 | Drug | 416.7 |
| 2 | Flavor(s) | q.s. |
| 3 | Colorant | q.s. |
| 4 | Preservative | q.s. |
| 5 | Buffering Agents | 28.3 |
| 6 | Saccharin | q.s. |
| 7. | PVP |  |
|   | To make | 1.0 g |

Mix Item Nos. 1, 2, 3, 4, 5, 6, and 7 well until uniform.

Part B (Reconstitution

Charge 6.0 g of above powder into a suitable container and add enough water to make up 100 ml. Shake well until uniform. Each 5 ml will then contain drug equivalent to 125 mg.

EXAMPLE 9

Oral Liquid

| Item No. | Ingredient | mg/ml |
|---|---|---|
| 1 | Drug | 25.0 |
| 2 | Sweetner | q.s. |
| 3 | Flavor | q.s. |
| 4 | Colorant | q.s. |
| 5 | Vegetable Oil | q.s. |
|   | To make | 1.0 ml |

Charge 90% of Item No. 5 needed into a suitable container. Charge Item Nos. 1, 2, 3 and 4 and mix well. Bring to the final volume by the reserved Item No. 5.

EXAMPLE 10

Suppository

| Item No. | Ingredient | Suppository |
|---|---|---|
| 1 | Drug | 125.0 |
| 2 | Witepsol H-15 | 1868 |

Melt Item No. 2 and blend Item No. 1 until uniform. Pour into mold and congeal in refrigerator. Remove suppository from mold.

We claim:

1. A biologically pure culture of the microorganism *Actinomadura brunnea* ATCC 39216, said culture being capable of producing 7-chloro-8-methoxy-2'-N-methyl-tetracycline in a recoverable quantity upon fermentation, under aerobic conditions in an aqueous medium containing assimilable sources of nitrogen and carbon.

* * * * *

UNITED STATES PATENT AND TRADEMARK OFFICE
CERTIFICATE OF CORRECTION

PATENT NO. : 5,183,758
DATED : February 2, 1993
INVENTOR(S) : Ann C. Horan It is certified that error appears in the above-identified patent and that said Letters Patent is hereby corrected as shown below:

On the Title page, item [54], line 2 and col. 1, line 2,

"7-CHLORO-3-METHOXY-2'-N-METHYLTET-"

should read

_ _ 7-CHLORO-8-METHOXY-2'-N-METHYLTET-_ _.

In line 4 of the title

"BRUNEA ATCC 39216"

should read

_ _ BRUNNEA ATCC 39216_ _.

Signed and Sealed this

Thirtieth Day of November, 1993

Attest:

BRUCE LEHMAN

*Attesting Officer*      *Commissioner of Patents and Trademarks*